US009701796B2

(12) United States Patent
Jung et al.

(10) Patent No.: US 9,701,796 B2
(45) Date of Patent: Jul. 11, 2017

(54) PREPARATION METHOD OF SUPERABSORBENT POLYMER

(71) Applicant: LG Chem, Ltd., Seoul (KR)

(72) Inventors: Hwayoon Jung, Daejeon (KR); Chang Sun Han, Daejeon (KR); Chul Hee Ryu, Daejeon (KR); Mi Young Kim, Daejeon (KR); Tae Bin Ahn, Daejeon (KR)

(73) Assignee: LG Chem, Ltd. (KR)

( * ) Notice: Subject to any disclaimer, the term of this patent is extended or adjusted under 35 U.S.C. 154(b) by 0 days.

(21) Appl. No.: 15/103,552

(22) PCT Filed: Dec. 5, 2014

(86) PCT No.: PCT/KR2014/011933
§ 371 (c)(1),
(2) Date: Jun. 10, 2016

(87) PCT Pub. No.: WO2015/088200
PCT Pub. Date: Jun. 18, 2015

(65) Prior Publication Data
US 2016/0311985 A1 Oct. 27, 2016

(30) Foreign Application Priority Data

Dec. 10, 2013 (KR) .......................... 10-2013-0153325
Dec. 4, 2014 (KR) .......................... 10-2014-0172998

(51) Int. Cl.
*C08F 2/46* (2006.01)
*C08F 2/50* (2006.01)
*C08G 61/04* (2006.01)
*C08J 3/24* (2006.01)
*C08F 2/10* (2006.01)
*C08J 3/075* (2006.01)
*C08F 2/48* (2006.01)
*C08F 220/06* (2006.01)
*A61L 15/60* (2006.01)
*A61L 15/24* (2006.01)
*A61L 26/00* (2006.01)
*C08J 3/07* (2006.01)
*C08J 3/12* (2006.01)

(52) U.S. Cl.
CPC .............. *C08J 3/245* (2013.01); *A61L 15/24* (2013.01); *A61L 15/60* (2013.01); *A61L 26/0014* (2013.01); *A61L 26/0061* (2013.01); *C08F 2/10* (2013.01); *C08F 2/48* (2013.01); *C08F 220/06* (2013.01); *C08J 3/07* (2013.01); *C08J 3/12* (2013.01); *C08J 3/075* (2013.01); *C08J 3/12* (2013.01); *C08J 2333/02* (2013.01); *C08J 2335/02* (2013.01)

(58) Field of Classification Search
CPC ........ C08J 3/245; C08J 3/075; C08J 2333/02; C08J 3/12; C08J 3/07; C08J 2335/02; A61L 26/0061; A61L 15/60; A61L 26/0014; A61L 15/24
USPC ........... 522/77, 74, 71, 6, 189, 184, 1; 520/1
See application file for complete search history.

(56) References Cited

U.S. PATENT DOCUMENTS

| 4,446,261 A | 5/1984 | Yamasaki et al. |
| 4,734,478 A | 3/1988 | Tsubakimoto et al. |
| 5,140,076 A | 8/1992 | Hatsuda et al. |
| 5,275,773 A * | 1/1994 | Irie ............................ C08J 3/12 264/141 |
| 5,669,894 A | 9/1997 | Goldman et al. |
| 6,849,665 B2 | 2/2005 | Frenz et al. |
| 7,816,301 B2 | 10/2010 | Ikeuchi et al. |
| 8,003,210 B2 | 8/2011 | Kobushi et al. |
| 8,697,812 B2 | 4/2014 | Won et al. |
| 2002/0165288 A1 | 11/2002 | Frenz et al. |
| 2005/0137546 A1* | 6/2005 | Joy .......................... A61L 15/60 604/368 |
| 2007/0135785 A1* | 6/2007 | Qin .......................... A61L 15/48 604/368 |
| 2007/0207924 A1 | 9/2007 | Ikeuchi et al. |
| 2008/0234420 A1 | 9/2008 | Smith et al. |
| 2008/0280154 A1 | 11/2008 | Kobushi et al. |
| 2009/0023848 A1* | 1/2009 | Ahmed .................... A61L 15/56 524/422 |
| 2009/0281232 A1 | 11/2009 | Ikeuchi et al. |
| 2011/0275513 A1* | 11/2011 | Tian ...................... C08F 220/06 502/402 |
| 2011/0301303 A1* | 12/2011 | Kim .......................... C08F 8/14 525/384 |

(Continued)

FOREIGN PATENT DOCUMENTS

EP  2557095 A1  2/2013
EP  2580256 A2  4/2013

(Continued)

OTHER PUBLICATIONS

International Search Report from PCT/KR2014/011933, dated Mar. 13, 2015.
Odian, George, "Principles of Polymerization," Second Edition, A Wiley-Interscience Publication, John Wiley & Sons, 1981, p. 203.
Schwalm, Reinhold, "UV Coatings: Basics, Recent Developments and New Applications." Elsevier Science (Dec. 21, 2016), p. 115.
Third Party Observation from PCT/KR2014/011933, dated Apr. 7, 2016.

(Continued)

*Primary Examiner* — Jessica E Whiteley
(74) *Attorney, Agent, or Firm* — Lerner, David, Littenberg, Krumholz & Mentlik, LLP

(57) ABSTRACT

Provided is a method of preparing a superabsorbent polymer. According to the method of preparing the superabsorbent polymer of the present invention, provided is a superabsorbent polymer having improved physical properties, in which the superabsorbent polymer has improved absorption rate and liquid permeability without reduction in centrifuge retention capacity or absorbency under load.

6 Claims, No Drawings

(56) References Cited

U.S. PATENT DOCUMENTS

| | | | |
|---|---|---|---|
| 2012/0267570 A1* | 10/2012 | Shi | A61L 15/60 252/194 |
| 2012/0296057 A1* | 11/2012 | Takaai | A61L 15/60 526/223 |
| 2014/0051813 A1 | 2/2014 | Won et al. | |
| 2014/0114035 A1 | 4/2014 | Nogi et al. | |
| 2015/0094427 A1* | 4/2015 | Lee | C08J 3/24 525/194 |
| 2015/0315321 A1* | 11/2015 | Won | A61L 15/22 525/328.8 |
| 2015/0376318 A1 | 12/2015 | Haag et al. | |
| 2016/0151531 A1* | 6/2016 | Lee | B01J 20/267 525/328.9 |
| 2016/0175813 A1* | 6/2016 | Ryu | C08J 3/075 502/402 |
| 2016/0207026 A1* | 7/2016 | Lee | C08J 3/245 |

FOREIGN PATENT DOCUMENTS

| | | |
|---|---|---|
| JP | S56161408 A | 12/1981 |
| JP | S57158209 A | 9/1982 |
| JP | 57-198714 A | 12/1982 |
| JP | 3145461 B2 | 3/2001 |
| JP | 3415036 B2 | 6/2003 |
| JP | 4315680 B2 | 8/2009 |
| JP | 4866733 B2 | 2/2012 |
| JP | 5367364 B2 | 12/2013 |
| KR | 19990051876 | 6/2000 |
| KR | 20030068198 A | 8/2003 |
| KR | 20100014556 A | 2/2010 |
| KR | 20110134333 A | 12/2011 |
| KR | 2012-0054836 A | 5/2012 |
| KR | 20120059169 A | 6/2012 |
| KR | 20130096152 A | 8/2013 |
| KR | 20130096218 A | 8/2013 |
| WO | 2006123561 A1 | 11/2006 |
| WO | 2009016055 A2 | 2/2009 |
| WO | 2012144595 A1 | 10/2012 |
| WO | 2014-112722 * | 7/2014 |
| WO | 2014118024 A1 | 8/2014 |

OTHER PUBLICATIONS

Written Opinion of the International Searching Authority from PCT/KR2014/011933, dated Mar. 13, 2015.

* cited by examiner

PREPARATION METHOD OF SUPERABSORBENT POLYMER

CROSS-REFERENCE TO RELATED APPLICATION

This application is a national phase entry under 35 U.S.C. §371 of International Application No. PCT/KR2014/011933, filed Dec. 5, 2014, which claims priority to Korean Patent Application No. 10-2013-0153325, filed Dec. 10, 2013 and Korean Patent Application No. 10-2014-0172998, filed Dec. 4, 2014, the disclosures of which are incorporated herein by reference.

BACKGROUND OF THE INVENTION (a) Field of the Invention

The present disclosure relates to a method of preparing a superabsorbent polymer, and more particularly, to a method of preparing a superabsorbent polymer, which may be used to obtain a superabsorbent polymer showing a high absorption rate and liquid permeability as well as a high centrifuge retention capacity.

(b) Description of the Related Art

A superabsorbent polymer (SAP) is a type of synthetic polymeric materials capable of absorbing moisture from 500 to 1000 times its own weight. Various manufacturers have denominated it as different names, such as SAM (Super Absorbency Material), AGM (Absorbent Gel Material), etc. Since such superabsorbent polymers started to be practically applied in sanitary products, now they have been widely used not only for hygiene products such as disposable diapers for children, etc., but also for water retaining soil products for gardening, water stop materials for the civil engineering and construction, sheets for raising seedling, fresh-keeping agents for food distribution fields, materials for poultice or the like.

As a preparation process for such superabsorbent polymers, a process by a reverse phase suspension polymerization and a process by a solution polymerization have been known. For example, Japanese Patent Laid-open Publication Nos. S56-161408, S57-158209, and S57-198714 disclose the reverse phase suspension polymerization.

The process by the solution polymerization further includes a thermal polymerization method in which a polymerization gel is polymerized while being broken and cooled in a kneader equipped with a plurality of shafts, and a photo-polymerization method in which an aqueous solution with a high concentration is irradiated with UV rays onto a belt to be polymerized and dried at the same time.

The hydrogel polymers thus obtained through the polymerization reaction are generally marketed in a powdery form after drying and pulverization processes.

In the products made of superabsorbent polymers, permeability is an index of determining fluidity of a liquid to be absorbed. Permeability may differ depending on the properties such as particle size distribution of crosslinked polymers, particle shape, and the connectedness of the open pores between particles, and surface modification of the swollen gel. Fluidity of the liquid passing through swollen particles differs depending on permeability of the superabsorbent polymer composition. A liquid cannot flow readily through the superabsorbent polymer composition with low permeability.

As one of the methods of increasing permeability of the superabsorbent polymer, there is a method of performing surface crosslinking reaction after polymerization, in which silica or clay is added together with a surface crosslinking agent. For example, U.S. Pat. Nos. 5,140,076 and 4,734,478 disclose the addition of silica during surface crosslinking of dry superabsorbent polymer powders.

However, permeability is improved by the addition of silica or clay, but there are problems that centrifuge retention capacity or absorbency under load is reduced in proportion thereto, and separation from the superabsorbent polymer easily occurs by external physical impact during transport.

Further, with the trend for slimness of hygiene products, a demand for a high absorption rate and liquid permeability as well as a high centrifuge retention capacity is increasing. However, these physical properties are conflicting with each other, and therefore, it is very difficult to satisfy all these properties.

SUMMARY OF THE INVENTION

In order to solve the above problems of the prior art, the present invention is intended to provide a method of preparing a superabsorbent polymer which exhibits a high absorption rate and liquid permeability as well as a high centrifuge retention capacity, thereby satisfying a demand for slimness of hygiene products.

To achieve the above object, the present invention provides a method of preparing a superabsorbent polymer, the method including the steps of:

performing thermal polymerization or photo-polymerization of a monomer composition including a water-soluble ethylene-based unsaturated monomer, an internal crosslinking agent, and a polymerization initiator to prepare a hydrogel polymer having a gel strength of 10,000 Pa to 13,000 Pa;

coarsely pulverizing the hydrogel polymer;

drying the coarsely pulverized hydrogel polymer;

pulverizing the dried polymer; and mixing the pulverized polymer and a surface crosslinking agent to perform a surface crosslinking reaction of the mixture.

According to the method of preparing the superabsorbent polymer of the present invention, provided is a superabsorbent polymer having improved physical properties, in which the superabsorbent polymer has improved absorption rate and liquid permeability without reduction in centrifuge retention capacity or absorbency under load. Therefore, it is possible to achieve a reduction of a fiber material ratio in the hygiene products and a reduction in thickness of the hygiene products, thereby satisfying the trend for slimness of hygiene products and improving satisfaction for convenience.

DETAILED DESCRIPTION OF THE EMBODIMENTS

The terminology used herein is for the purpose of describing exemplary embodiments only and is not intended to limit the present invention. The singular forms may be intended to include the plural forms as well, unless the context clearly indicates otherwise. It will be understood that the terms "comprise", "include", and "have" when used herein specify the presence of stated features, steps, components, or combinations thereof, but do not preclude the presence or addition of one or more other features, steps, components, or combinations thereof.

While the present invention is susceptible to various modifications and alternative forms, specific embodiments will be illustrated and described in detail as follows. It should be understood, however, that the description is not intended to limit the present invention to the particular forms disclosed, but on the contrary, the intention is to cover all modifications, equivalents, and alternatives falling within the spirit and scope of the invention.

Hereinafter, a method of preparing a superabsorbent polymer according to a specific embodiment of the present invention will be described in more detail.

A method of preparing a superabsorbent polymer according to an embodiment of the present invention may include the steps of:

performing thermal polymerization or photo-polymerization of a monomer composition including a water-soluble ethylene-based unsaturated monomer, an internal crosslinking agent, and a polymerization initiator to prepare a hydrogel polymer having a gel strength of 10,000 Pa to 13,000 Pa;

coarsely pulverizing the hydrogel polymer;

drying the coarsely pulverized hydrogel polymer;

pulverizing the dried polymer; and mixing the pulverized polymer and a surface crosslinking agent to perform a surface crosslinking reaction of the mixture.

The present inventors have continued to study a superabsorbent polymer showing a high absorption rate and liquid permeability while having a high centrifuge retention capacity, and they found that when a hydrogel polymer as a base resin of the superabsorbent polymer has a gel strength satisfying a predetermined range, and process conditions for coarse pulverization of the hydrogel polymer are optimized, it is possible to improve physical properties of a final superabsorbent polymer, thereby producing hygiene products, to which an ultra-thin technology is applied, leading to the present invention.

In the method of preparing the superabsorbent polymer of the present invention, the monomer composition which is a raw material of the superabsorbent polymer includes a water-soluble ethylene-based unsaturated monomer, an internal crosslinking agent, and a polymerization initiator.

As the water-soluble ethylene-based unsaturated monomer, any monomer may be used without limitation, as long as the monomer is generally used in the preparation of the superabsorbent polymer. Herein, any one or more monomers selected from the group consisting of an anionic monomer and salts thereof, a nonionic hydrophilic monomer and an amino group-containing unsaturated monomer, and a quaternary compound thereof may be used.

Specifically, any one or more selected from the group consisting of an anionic monomer such as (meth)acrylic acid, maleic anhydride, fumaric acid, crotonic acid, itaconic acid, 2-acryloylethane sulfonic acid, 2-methacryloylethane sulfonic acid, 2-(meth)acryloylpropane sulfonic acid, or 2-(meth)acrylamide-2-methyl propane sulfonic acid, and salts thereof; a nonionic hydrophilic monomer such as (meth)acrylamide, N-substituted (meth)acrylate, 2-hydroxyethyl(meth)acrylate, 2-hydroxypropyl(meth)acrylate, methoxy polyethylene glycol (meth)acrylate, or polyethylene glycol (meth)acrylate; and an amino group-containing unsaturated monomer such as (N,N)-dimethylaminoethyl (meth)acrylate or (N,N)-dimethylaminopropyl(meth)acrylamide, and a quaternary compound thereof may be used.

More preferably, acrylic acid or salts thereof, for example, acrylic acid or alkali metal salts such as sodium salts thereof may be used, and it is possible to prepare a superabsorbent polymer having superior physical properties by using these monomers. When the alkali metal salt of acrylic acid is used as the monomer, acrylic acid may be used after being neutralized with a basic compound such as caustic soda (NaOH). More specifically, the acrylic acid may be neutralized at about 50 mol % or more, about 60 mol % or more, or about 70 mol % or more, thereby more effectively achieving the physical properties of the superabsorbent polymer of the present invention. That is, in the water-soluble ethylene-based unsaturated monomer, a neutralization degree of the acidic groups may be about 50 mol % or more.

The concentration of the water-soluble ethylene-based unsaturated monomer may be about 20% by weight to about 60% by weight, preferably about 40% by weight to about 50% by weight, based on the monomer composition including the raw materials of the superabsorbent polymer and a solvent, and the concentration may be properly controlled, considering polymerization time and reaction conditions. However, if the monomer concentration is too low, the yield of the superabsorbent polymer may become low and an economic problem may occur. On the contrary, if the concentration is too high, there is a process problem that a part of the monomers is precipitated, or pulverization efficiency is lowered upon pulverization of the polymerized hydrogel polymer, and the physical properties of the superabsorbent polymer may be reduced.

In the method of preparing the superabsorbent polymer of the present invention, the internal crosslinking agent used upon polymerization may be a compound having a cure dose of about 80% to about 200%, when a cure dose of the water-soluble ethylene-based unsaturated monomer is regarded as 100%, in terms of internal crosslinking uniformity. Preferably, the internal crosslinking agent may be a compound having a cure dose of about 90% to about 180%, and more preferably a cure dose of about 95% to about 170%, based on 100% of the cure dose of the water-soluble ethylene-based unsaturated monomer.

For example, when acrylic acid (AA) is used as the water-soluble ethylene-based unsaturated monomer, the internal crosslinking agent may be a compound having a cure dose of about 160 mJ/cm$^2$ to about 400 mJ/cm$^2$, preferably about 180 mJ/cm$^2$ to about 360 mJ/cm$^2$, and more preferably about 190 mJ/cm$^2$ to about 340 mJ/cm$^2$, because the cure dose of acrylic acid is about 200 mJ/cm$^2$.

Here, the cure dose means the amount of energy required to cure. That is, as the number of the cure dose increases, the amount of energy required to cure is increased. The values representing the cure dose may be measured using a light meter. For example, a lamp of a curing machine with accessories is set at a predetermined luminance, and a sample is loaded on the belt of the curing machine and passed through the UV curing machine. In this regard, the number of passage through the curing machine is evaluated, based on the conveyor speed of the curing machine and light intensity, and total energy after curing of the surface is calculated. Therefore, there is no limitation in the amount of the sample when the cure dose is measured. In a more specific embodiment, upon the measurement, the solution is poured into a 100 mm-Petri dish at a thickness of 0.5 cm, which is loaded on the conveyor belt, followed by operation of the belt.

The cure doses of the several materials among acrylate-based hydrocarbon compounds are as shown in Table 1 below.

TABLE 1

| Acrylate-based hydrocarbon | Number of acrylic functional group | Cure dose (unit: mJ/cm$^2$) | Percentage of cure dose to acrylic acid (%) |
|---|---|---|---|
| PEGDA | 2 | 200 | 100 |
| HDDA | 2 | 320 | 160 |

TABLE 1-continued

| Acrylate-based hydrocarbon | Number of acrylic functional group | Cure dose (unit: mJ/cm$^2$) | Percentage of cure dose to acrylic acid (%) |
|---|---|---|---|
| TMP(PO)3TA | 3 | 490 | 245 |
| PETTA | 4 | 158 | 79 |
| NPG(PO)2DA | 2 | 153 | 76.5 |
| TMP(EO)9TA | 3 | 200 | 100 |

PEGDA: Polyethyleneglycol diacrylate
HDDA: Hexanediol diacrylate
TMP(PO)3TA: 3 mol % propoxylated TMPTA (Trimethylolpropane triacrylate)
PETTA: Pentaerythritol Triacrylate
NPG(PO)2DA: 2 mol % propoxylated Neopentylglycol Diacrylate
TMP(EO)9TA: 9 mol % ethoxylated TMPTA (Trimethylolpropane triacrylate)
* Cure dose of acrylic acid: 200 mJ/cm$^2$
* Cure dose information provider: Miwon Specialty Chemical Co., Ltd.

Referring to the cure doses of the materials of Table 1, an acrylate-based hydrocarbon compound suitable for the method of preparing the superabsorbent polymer of the present invention may be selected and used as the internal crosslinking agent. However, the internal crosslinking agent usable in the preparation method of the present invention is not limited to the materials exemplified in Table 1, and any material may be used without limitation, as long as it is a material satisfying the above range of the relative cure dose to the cure dose of the water-soluble ethylene-based unsaturated monomer, as described above.

According to an embodiment of the present invention, among various acrylate-based hydrocarbon compounds, a compound having a cure dose of about 80% to about 200%, preferably about 90% to about 180%, and more preferably about 95% to about 170%, based on 100% of the cure dose of the water-soluble ethylene-based unsaturated monomer is used as the internal crosslinking agent, and more preferably, two or more compounds having a cure dose within the above range are mixed and used, thereby obtaining a hydrogel polymer having a gel strength ranging from about 10,000 Pa to about 13,000 Pa.

According to an embodiment of the present invention, the internal crosslinking agent is included at a concentration of about 4,000 ppm to about 7,500 ppm, preferably about 4,500 ppm to about 7,000 ppm, and more preferably about 5,000 ppm to about 6,500 ppm, based on the total weight of the water-soluble ethylene-based unsaturated monomer included in the monomer composition. When the concentration of the internal crosslinking agent satisfies the above range, a superabsorbent polymer having more optimized physical properties while satisfying the gel strength of about 10,000 Pa to about 13,000 Pa may be prepared.

Further, when two or more kinds of the internal crosslinking agents are mixed and used, their concentrations may be adjusted according to the cure dose of the respective internal crosslinking agents to be mixed and used, as long as the total concentration of the internal crosslinking agents is within the above range.

More specifically, the concentrations of the respective internal crosslinking agents may be adjusted so that the sum of the cure dose (unit: J/cm$^2$) of respective internal crosslinking agent multiplied by the concentration of the corresponding internal crosslinking agent (concentration with respect to the total weight of the water-soluble ethylene-based unsaturated monomer, unit: ppm) is about 800 to about 1,800, preferably about 800 to about 1,600, and more preferably about 1,000 to about 1,500.

In the method of preparing the superabsorbent polymer of the present invention, the polymerization initiator used in polymerization is not particularly limited, as long as it is generally used in the preparation of the superabsorbent polymer.

Specifically, the polymerization initiator may be a thermal polymerization initiator or a photo-polymerization initiator by UV irradiation, depending on a polymerization method. However, even though the photo-polymerization is performed, a certain amount of heat may be generated by UV irradiation or the like, and also generated with exothermic polymerization reaction. Therefore, the thermal polymerization initiator may be further included.

As the photo-polymerization initiator, a compound capable of forming radicals by a light such as UV may be used without limitations in the constitution.

For example, one or more selected from the group consisting of benzoin ether, dialkyl acetophenone, hydroxyl alkylketone, phenyl glyoxylate, benzyl dimethyl ketal, acyl phosphine, and α-aminoketone may be used as the photo-polymerization initiator. Meanwhile, as the specific example of acyl phosphine, commercial Lucirin TPO, namely, 2,4,6-trimethyl-benzoyl-trimethyl phosphine oxide may be used. More various photo-polymerization initiators are well disclosed in "UV Coatings: Basics, Recent Developments and New Application (Elsevier, 2007)" written by Reinhold Schwalm, p 115, however, they are not limited to the above described examples.

The concentration of the photo-polymerization initiator may be about 0.01% by weight to about 1.0% by weight, based on the total weight of the monomer composition. If the concentration of the photo-polymerization initiator is too low, the polymerization rate may become low. If the concentration of the photo-polymerization initiator is too high, the molecular weight of the superabsorbent polymer may become low and its physical properties may be not uniform.

Further, one or more selected from the group consisting of persulfate-based initiators, azo-based initiators, hydrogen peroxide and ascorbic acid may be used as the thermal polymerization initiator. Specific examples of the persulfate-based initiators may include sodium persulfate ($Na_2S_2O_8$), potassium persulfate ($K_2S_2O_8$), ammonium persulfate (($NH_4)_2S_2O_8$) or the like. Examples of the azo-based initiators may include 2,2-azobis(2-amidinopropane)dihydrochloride, 2,2-azobis-(N,N-dimethylene)isobutyramidine dihydrochloride, 2-(carbamoylazo)isobutylonitril, 2,2-azobis(2-[2-imidazolin-2-yl]propane)dihydrochloride, 4,4-azobis-(4-cyanovaleric acid) or the like. More various thermal polymerization initiators are well-disclosed in 'Principle of Polymerization (Wiley, 1981)' written by Odian, p 203, however, they are not limited to the above described examples.

The concentration of the thermal polymerization initiator may be about 0.001% by weight to about 0.5% by weight, based on the total weight of the monomer composition. If the concentration of the thermal polymerization initiator is too low, additional thermal polymerization hardly occurs, and thus the addition effect of the thermal polymerization initiator may not be sufficiently obtained. If the concentration of the thermal polymerization initiator is too high, the molecular weight of the superabsorbent polymer may become low and its physical properties may be not uniform.

In the preparation method of the present invention, the monomer composition of the superabsorbent polymer may further include an additive such as a thickener, a plasticizer, a preservation stabilizer, an antioxidant, etc., if necessary.

The raw materials such as the above-described water-soluble ethylene-based unsaturated monomer, photo-polymerization initiator, thermal polymerization initiator, internal crosslinking agent, and additive may be prepared in the form of a solution of the monomer composition which is dissolved in a solvent.

In this regard, as the solvent, any solvent may be used without limitations in the constitution as long as it is able to dissolve the above ingredients, and for example, one or more selected from water, ethanol, ethylene glycol, diethylene glycol, triethylene glycol, 1,4-butanediol, propylene glycol, ethylene glycol monobutyl ether, propylene glycol monomethyl ether, propylene glycol monomethyl ether acetate, methyl ethyl ketone, acetone, methyl amyl ketone, cyclohexanone, cyclopentanone, diethylene glycol monomethyl ether, diethylene glycol ethylether, toluene, xylene, butyrolactone, carbitol, methyl cellosolve acetate and N,N-dimethylacetamide may be used in combination.

The solvent may be included in a residual amount of excluding the above described components from the total weight of the monomer composition.

Meanwhile, the method for forming the hydrogel polymer by thermal polymerization or photo-polymerization of the monomer composition is not particularly limited in the constitution, as long as it is a method generally used.

Specifically, the polymerization method is largely classified into the thermal polymerization and the photo-polymerization according to the polymerization energy source. The thermal polymerization may be carried out in a reactor like a kneader equipped with agitating spindles and the photo-polymerization may be carried out in a reactor equipped with a movable conveyor belt. The above-described polymerization method is an example only, and the present invention is not limited thereto.

For example, the polymerization process may be performed at about 35° C. or higher, or at about 35° C. to about 90° C. by thermal polymerization, together with photo-polymerization by UV irradiation in the range of about 100 nm to about 400 nm.

For example, as described above, thermal polymerization is performed by providing hot air to a reactor like a kneader equipped with the agitating spindles or by heating the reactor to obtain the hydrogel polymer. At this time, the hydrogel polymer thus obtained may have the size of centimeters or millimeters when it is discharged from the outlet of the reactor, according to the type of agitating spindles equipped in the reactor. Specifically, the hydrogel polymer may be obtained in various forms according to the concentration of the monomer composition fed thereto, the feeding speed, or the like. Generally, the hydrogel polymer having a weight average particle size of 2 mm to 50 mm may be obtained.

Further, as described above, when the photo-polymerization is carried out in a reactor equipped with a movable conveyor belt, the hydrogel polymer generally obtained may be a hydrogel polymer in a sheet-type having a width of the belt. In this regard, the thickness of the polymer sheet may vary according to the concentration of the monomer composition fed thereto and the feeding speed, and the feeding speed of the monomer composition is preferably controlled so that the polymer sheet having a thickness of about 0.5 cm to about 5 cm is obtained. If the monomer composition is fed so that the thickness of the sheet-type polymer becomes too thin, the production efficiency becomes low, which is not preferred. If the thickness of the sheet-type polymer exceeds 5 cm, the polymerization reaction may not uniformly occur throughout the polymer due to the excessively high thickness.

In the method of preparing the superabsorbent polymer of the present invention, the hydrogel polymer may be preferably formed by photo-polymerization.

In this regard, the hydrogel polymer thus obtained by the method may have generally a water content of about 40% by weight to about 80% by weight. Meanwhile, the term "water content", as used herein, means a water content in the total weight of the hydrogel polymer, which is obtained by subtracting the weight of the dry polymer from the weight of the hydrogel polymer. Specifically, the water content is defined as a value calculated by measuring the weight loss according to evaporation of water in the polymer during the drying process of increasing the temperature of the polymer with infrared heating. In this regard, the water content is measured under the drying conditions which are determined as follows; the temperature is increased from room temperature to about 180° C. and then the temperature is maintained at 180° C., and the total drying time is determined as 20 minutes, including 5 minutes for the temperature rising step.

Polymerization is performed by the above-described method to obtain a hydrogel polymer having a gel strength ranging from about 10,000 Pa to about 13,000 Pa, or about 10,500 Pa to about 12,800 Pa, or about 10,500 Pa to about 12,600 Pa. The gel strength is an index of evaluating the crosslinking degree of polymers, and as the gel strength is higher, the polymerized hydrogel polymer may have a higher crosslinking density. Meanwhile, if the gel strength of the hydrogel polymer is too low or too high out of the above range, water-soluble components may be excessively generated or damage of the hydrogel polymer may occur in the subsequent coarse pulverization step, and therefore, there is a problem that it is difficult to achieve sufficient centrifuge retention capacity and absorption rate.

According to the method of preparing the superabsorbent polymer of the present invention, when the gel strength of the hydrogel polymer before coarse pulverization satisfies the above range by controlling polymerization conditions, and process conditions of the after-mentioned coarse pulverization are optimized, an excellent superabsorbent polymer having balanced physical properties, that is, showing synergistic effects of excellent centrifuge retention capacity (CRC), absorbency under load (AUP), liquid permeability (SFC), and absorption rate (FSR) may be prepared.

Next, the step of coarsely pulverizing the obtained hydrogel polymer is performed.

The coarse pulverization step may be performed by injecting the hydrogel polymer into a chopper, etc. to extrude it through an outlet having a plurality of holes having a predetermined size or a perforated panel. In this regard, an extruder used for extruding the hydrogel polymer may be a single- or multi-screw extruder.

When the hydrogel polymer is coarsely pulverized by extruding the hydrogel polymer into the outlet having holes, a predetermined pressure is applied to the hydrogel polymer, and therefore, the intrinsic gel strength and morphology of the hydrogel polymer may be changed by the pressure, and the surface area is increased. In this regard, physical properties of the polymer after the coarse pulverization step may differ according to the diameter of the hole. For example, as the diameter of the hole is smaller, the pressure applied to the hydrogel polymer is increased and the surface area is increased, resulting in a high absorption rate, but the possibility of damaging the hydrogel polymer may be increased to reduce centrifuge retention capacity and to increase residual monomers. Therefore, it is not easy to determine coarse pulverization conditions which are optimized for a superabsorbent polymer having balanced physical properties of a high centrifuge retention capacity and a high absorption rate.

Accordingly, based on the research results of the present inventors, it was confirmed that when the gel strength (unit: Pa) of the hydrogel polymer before coarse pulverization and the diameter (unit: mm) of holes formed in the outlet or the perforated panel for coarse pulverization of the hydrogel polymer in the coarse pulverization step satisfy the following Formula 1, the final superabsorbent polymer exhibits optimized physical properties.

$$1140*x+730 \leq y < 600*x+8400 \qquad \text{[Formula 1]}$$

wherein x is the diameter of the hole (unit: mm) and y is the gel strength (unit: Pa) of the hydrogel polymer before coarse pulverization.

According to an embodiment of the present invention, the hole may have a diameter of about 6.5 mm to about 10 mm within a range satisfying the above Formula 1. If the hole has a diameter of 6.5 mm or less, agglomeration between particles may occur or a large amount of residual monomers may be generated during the pulverization process. If the hole has a very large diameter of more than 10 mm, the surface may be irregularly contracted during the subsequent drying process, and therefore, the final resin may not have uniform quality. Therefore, when the hydrogel polymer having the gel strength within the above range is coarsely pulverized to have a diameter within the above range, and then dried and pulverized, a small amount of residual monomers is generated and the polymer has a proper roughness on the surface, thereby increasing absorption rate of the final superabsorbent polymer.

Next, the hydrogel polymer thus coarsely pulverized is subjected to a drying process. In this regard, the drying temperature of the drying step may be about 150° C. to about 250° C. When the drying temperature is lower than 150° C., there is a concern about excessively long drying time or deterioration of the physical properties of the superabsorbent polymer finally formed, and when the drying temperature is higher than 250° C., only the surface of the polymer is dried, and thus there is a concern about generation of fine powder during the subsequent pulverization process and deterioration of the physical properties of the superabsorbent polymer finally formed. Therefore, the drying process may be preferably performed at a temperature of about 150° C. to about 200° C., and more preferably about 160° C. to about 180° C.

Meanwhile, the drying process may be carried out for about 20 to about 90 minutes, considering the process efficiency, but is not limited thereto.

Furthermore, any known drying method may be selected and used in the drying step without limitation, if it can be generally used for drying the hydrogel polymer. Specifically, the drying step may be carried out by a method of supplying hot air, irradiating infrared rays, irradiating microwaves, irradiating ultraviolet rays or the like. When the drying step as above is finished, the water content of the polymer may be about 0.1% by weight to about 10% by weight.

Next, the dried polymer obtained from the drying step is subjected to a pulverization step.

The polymer powder obtained from the pulverization step may have a particle size of about 150 μm to about 850 μm. Specific example of a milling device used to produce the polymer having a particle size within the above range may include a pin mill, a hammer mill, a screw mill, a roll mill, a disc mill, a jog mill or the like, but the present invention is not limited to the above-described examples.

To control the physical properties of the superabsorbent polymer powder finally manufactured after the pulverization step, the polymer powder obtained after pulverization may be subjected to an additional process of classifying the polymer powder according to the particle size. Only a polymer having a particle size of about 150 μm to about 850 μm is preferably sieved and then selectively applied to the surface crosslinking reaction and finally manufactured.

Next, surface crosslinking reaction is performed by mixing the pulverized polymer with a surface crosslinking agent.

The surface crosslinking is a step of increasing the crosslinking density in the vicinity of the surface of the superabsorbent polymer particle with regard to the internal crosslinking density of particles. In general, the surface crosslinking agent is applied to the surface of the superabsorbent polymer particle. Therefore, this reaction occurs on the surface of the superabsorbent polymer particle, which improves crosslinking on the surface of the particle without substantially affecting the interior of the particle. Thus, the surface-crosslinked superabsorbent polymer particles have a higher level of crosslinking in the vicinity of the surface than in the interior.

In this regard, a compound capable of reacting with the functional groups of the polymer may be used as the surface crosslinking agent without limitations in the constitution.

To improve the properties of the produced superabsorbent polymer, one or more selected from the group consisting of a polyhydric alcohol compound; an epoxy compound; a polyamine compound; a haloepoxy compound; a condensation product of the haloepoxy compound; an oxazoline compound; a mono-, di-, or polyoxazolidinone compound; a cyclic urea compound; a polyvalent metal salt; and an alkylene carbonate compound may be preferably used as the surface crosslinking agent.

Specific examples of the polyhydric alcohol compound may be one or more selected from the group consisting of a mono-, di-, tri-, tetra-, or polyethylene glycol, monopropylene glycol, 1,3-propanediol, dipropylene glycol, 2,3,4-trimethyl-1,3-pentanediol, polypropylene glycol, glycerol, polyglycerol, 2-butene-1,4-diol, 1,4-butanediol, 1,3-butanediol, 1,5-pentanediol, 1,6-hexanediol, and 1,2-cyclohexane dimethanol.

Further, the epoxy compound may be ethylene glycol diglycidyl ether, glycidol, etc., and the polyamine compound may be one or more selected from the group consisting of ethylene diamine, diethylene triamine, triethylene tetraamine, tetraethylene pentamine, pentaethylene hexamine, polyethylene imine, and polyamide polyamine.

Further, the haloepoxy compound may be epichlorohydrin, epibromohydrin, or α-methylephichlorohydrin. Meanwhile, the mono-, di-, or polyoxazolidinone compound may be, for example, 2-oxazolidinone.

Further, the alkylene carbonate compound may be ethylene carbonate, etc. These compounds may be used singly or in combination. On the other hand, to increase the efficiency of the surface crosslinking process, one or more of polyhydric alcohols are preferably included in these surface crosslinking agents. More preferably, polyhydric alcohol compounds having 2 to 10 carbon atoms may be used.

With regard to the method of adding the surface crosslinking solution to the polymer, there is no limitation in the constitution. A method of adding and mixing the surface crosslinking solution and the polymer powder in a reactor, a method of spraying the surface crosslinking solution onto the polymer powder, or a method of continuously feeding the polymer and the surface crosslinking solution to a mixer which is continuously operated may be used.

The surface crosslinking agent may be added in the form of a surface crosslinking solution by mixing it with additional water and alcohol. When water and alcohol are added, it is advantageous in that the surface crosslinking agent may be evenly dispersed in the polymer. In this regard, the amount of water and alcohol added thereto may be, but is not particularly limited to, preferably about 2 parts by weight to about 20 parts by weight, based on 100 parts by weight of the polymer for the purpose of inducing uniform dispersion of the surface cross-linking agent, preventing agglomeration of the polymer powder, and optimizing the surface penetrating depth of the cross-linking agent at the same time.

The surface crosslinking reaction is allowed to occur by heating the surface crosslinking agent-added polymer particles at about 150° C. to about 220° C., preferably at about 165° C. to about 210° C. for about 15 minutes to about 80 minutes, and preferably for about 20 minutes to about 70 minutes. If the crosslinking reaction temperature is lower than 150° C., sufficient surface crosslinking reaction may not occur, and if the crosslinking reaction temperature is higher than 220° C., the surface crosslinking reaction may occur excessively. Further, if the crosslinking reaction time is shorter than 15 minutes, sufficient surface crosslinking reaction may not occur, and if the crosslinking reaction time is longer than 80 minutes, the surface crosslinking reaction may occur excessively to excessively increase the crosslinking density of the particle surface, leading to deterioration in physical properties.

A means for raising the temperature for surface crosslinking reaction is not particularly limited. Heating may be performed by providing a heating medium or by directly providing a heat source. In this regard, the type of the heating medium applicable may be a hot fluid such as steam, hot air, hot oil, or the like. However, the present invention is not limited thereto. The temperature of the heating medium provided may be properly controlled, considering the means of the heating medium, the heating rate, and the target temperature. Meanwhile, as the heat source provided directly, an electric heater or a gas heater may be used, but the present invention is not limited to these examples.

The total content of the surface crosslinking agent in the surface crosslinking solution may be properly controlled according to the type of the surface crosslinking agent or reaction conditions, and the content of the surface crosslinking agent is preferably about 0.01 parts by weight to about 10 parts by weight, preferably about 0.01 parts by weight to about 5 parts by weight, based on 100 parts by weight of the pulverized polymer. If the content of the surface crosslinking agent is too low, surface crosslinking reaction may hardly occur, and if the content of the surface crosslinking agent is too high, excessive surface crosslinking reaction may occur, leading to deterioration in absorption ability and physical properties.

The superabsorbent polymer obtained according to the preparation method of the present invention has improved centrifuge retention capacity, liquid permeability, and absorption rate, in which these physical properties are balanced. Therefore, it is possible to obtain a superabsorbent polymer showing high transparency and absorption rate without reduction in centrifuge retention capacity.

As described above, the present invention provides combinations of physical properties for optimizing centrifuge retention capacity (CRC), absorbency under load (AUL), liquid permeability (SFC), and absorption rate (FSR) of the superabsorbent polymer at the same time, thereby obtaining synergistic effects, leading to balanced physical properties. Accordingly, it is possible to obtain a superabsorbent polymer showing high transparency and absorption rate without reduction in centrifuge retention capacity. The superabsorbent polymer of the present invention may be applied to production of hygiene products, thereby inducing excellent physical properties and comfortable wearing sensation.

In this regard, centrifuge retention capacity (CRC) is a value measured in accordance with EDANA method WSP 241.2, and absorbency under load (AUL) is a value measured in accordance with EDANA method WSP 242.2.

Further, liquid permeability (SFC: Saline Flow Conductivity) may be measured in accordance with a method described in U.S. Pat. No. 5,669,894. Absorption rate or free swell rate (FSR) may be measured in accordance with International Patent Publication NO. WO 2009/016055.

Centrifuge retention capacity (CRC) of the superabsorbent polymer for a physiological saline solution may be calculated according to the following Equation 1:

$$CRC(g/g) = \{[W_2(g) - W_1(g)]/W_0(g)\} - 1 \qquad \text{[Equation 1]}$$

wherein $W_0(g)$ is the weight (g) of the superabsorbent polymer, $W_1(g)$ is the weight of the apparatus, which is measured after draining water off at 250 G for 3 minutes using a centrifuge without the superabsorbent polymer, and $W_2(g)$ is the weight of the apparatus including the superabsorbent polymer, which is measured after immersing the superabsorbent polymer in 0.9 wt % physiological saline solution at room temperature for 30 minutes and draining water off at 250 G for 3 minutes using a centrifuge. In particular, $W_0(g)$ as the weight of the superabsorbent polymer may be the weight of the superabsorbent polymer having a size of 300 to 600 micrometers (μm), which is obtained by sieving.

The centrifuge retention capacity (CRC) of the superabsorbent polymer for the physiological saline solution may be 25 g/g or more, preferably about 26 g/g or more, and more preferably about 27 g/g or more, for example, about 25 g/g to about 34 g/g, or about 25 g/g to about 32 g/g, or about 26 g/g to about 30 g/g. If the centrifuge retention capacity (CRC) for the physiological saline solution is less than 25 g/g, there is a problem that centrifuge retention capacity of final products such as hygiene products is reduced to deteriorate physical properties of the final products.

Further, with regard to the superabsorbent polymer of the present invention, the absorbency under load (AUL) of 0.9 psi in the physiological saline solution may be calculated by the following Equation 2:

$$AUL(g/g) = [W_4(g) - W_3(g)]/W_0(g) \qquad \text{[Equation 2]}$$

wherein $W_0(g)$ is the weight (g) of the superabsorbent polymer, $W_3(g)$ is the sum of the weight of the superabsorbent polymer and the weight of the apparatus capable of providing a load for the superabsorbent polymer, and $W_4(g)$ is the sum of the weight of the water-absorbed superabsorbent polymer after supplying water for the superabsorbent polymer under a load (0.9 psi) for 1 hour and the weight of the apparatus capable of providing a load for the superabsorbent polymer.

For example, the absorbency under load (AUL) of 0.9 psi may be measured by placing 0.16 g of the superabsorbent polymer having a size of 300 to 600 micrometers (μm), which is obtained by sieving, in a kit for measuring absorbency under load (AUL), and then swelling the polymer under load in a 0.9% saline solution for 1 hour while putting a weight of 0.9 psi thereon. At this time, the cell is weighed after 1 hour to determine absorbency under load (AUL). In this case, $W_0(g)$ as the weight of the superabsorbent polymer may be the weight of the superabsorbent polymer having a size of 300 to 600 micrometers (μm), which is obtained by sieving.

With regard to the superabsorbent polymer, its absorbency under load (AUL) of 0.9 psi may be 20 g/g or more, preferably about 22 g/g or more, and more preferably, about 23 g/g or more, for example, about 20 g/g to about 32 g/g, or about 22 g/g to about 30 g/g, or about 23 g/g to about 28 g/g. It is preferable that the superabsorbent polymer has higher absorbency under load. However, since absorbency under load is a physical property conflicting to centrifuge retention capacity, the centrifuge retention capacity may be reduced by excessively increasing the absorbency under load. It is important to improve absorbency under load and centrifuge retention capacity at the same time.

In the present invention, $W_0(g)$ described in Equations 1 to 2 corresponds to the weight (g) of the superabsorbent polymer, which is applied to each of the physical properties, and they may be the same as or different from each other.

With regard to the superabsorbent polymer of the present invention, the liquid permeability (SFC) may be measured and calculated according to U.S. Pat. No. 5,669,894.

The liquid permeability (SFC) of the superabsorbent polymer may be about $70*10^{-7}$ cm$^3$*sec/g or more, preferably about $80*10^{-7}$ cm$^3$*sec/g or more, and more preferably about $90*10^{-7}$ cm$^3$*sec/g or more, for example, about $70*10^{-7}$ cm$^3$*sec/g to about $150*10^{-7}$ cm$^3$*sec/g, or about $80*10^{-7}$ cm$^3$*sec/g to about $140*10^{-7}$ cm$^3$*sec/g, or about $90*10^{-7}$ cm$^3$*sec/g to about $130*10^{-7}$ cm$^3$*sec/g. The liquid permeability (SFC) is a value of evaluating fluidity of a liquid to be absorbed into the superabsorbent polymer. If the liquid permeability (SFC) is less than $70*10^{-7}$ cm$^3$*sec/g, absorbency under load may be reduced to deteriorate physical properties of the final product.

With regard to the superabsorbent polymer of the present invention, the absorption rate (FSR) may be measured and calculated according to International Patent Publication NO. WO 2009/016055.

The absorption rate (FSR) of the superabsorbent polymer for physiological saline solution may be about 0.25 g/g/s or more, preferably about 0.27 g/g/s or more, and more preferably about 0.30 g/g/s or more, for example, about 0.25 g/g/s to about 0.5 g/g/s, or about 0.27 g/g/s to about 0.5 g/g/s, or about 0.27 g/g/s to about 0.45 g/g/s. The absorption rate (FSR) is a value of evaluating free swell rate of the superabsorbent polymer. If the absorption rate (FSR) is less than 0.25 g/g/s, absorption rate of the final product may be reduced to deteriorate physical properties of final products.

As described above, the superabsorbent polymer obtained according to the preparation method of the present invention exhibits a high absorption rate and liquid permeability under pressure while having centrifuge retention capacity and absorbency under load at a predetermined level, in which these physical properties are balanced. In general, as the superabsorbent polymer has high liquid permeability, centrifuge retention capacity and absorbency under load tend to decrease. That is, if the superabsorbent polymer has high crosslinking degree and high strength, the centrifuge retention capacity is high, but the liquid permeability and absorption rate are low. In contrast, if the superabsorbent polymer has high liquid permeability and high absorption rate, the centrifuge retention capacity is relatively low, and thus it is difficult to increase centrifuge retention capacity and liquid permeability at the same time.

However, the superabsorbent polymer obtained according to the preparation method of the present invention has improved absorption rate and liquid permeability without reduction in centrifuge retention capacity or absorbency under load, and therefore, the present invention provides the superabsorbent polymer having improved physical properties.

Accordingly, since conflicting physical properties of centrifuge retention capacity and permeability are balanced, the superabsorbent polymer may be very properly used as a filler of thin or ultra thin hygiene products.

Hereinafter, the present invention will be described in more detail with reference to the following Examples. However, the following Examples are for illustrative purposes only, and the present invention is not intended to be limited by these Examples.

EXAMPLE

Example 1

450 g of acrylic acid was mixed with 8 g of 0.5 wt % IRGACURE 819 initiator diluted in acrylic acid in a 2 L-glass reactor surrounded by a jacket through which a heating medium pre-cooled at 25° C. was circulated, and 50 g of 5 wt % polyethylene glycol diacrylate (PEGDA, molecular weight of 598 g/mol, Cure Dose of 200 mJ/cm$^2$) diluted with acrylic acid was injected, and 10 g of 5 wt % 1,6-hexanediol diacrylate (molecular weight of 226 g/mol, Cure Dose of 320 mJ/cm$^2$) diluted with acrylic acid was injected, and then 660 g of 32 wt % caustic soda solution was slowly added dropwise.

After confirming that the temperature of the mixture increased to 80° C. or higher by neutralization heat generated upon mixing the two solutions, the mixture was left until reaction temperature reached 40° C. When reaction temperature reached 40° C., 50 g of 2% sodium persulfate solution diluted with water was injected.

The solution was poured in a Vat-type tray (15 cm in width×15 cm in length) installed in a square polymerizer which had a light irradiation device installed at the top and was preheated to 80° C., and photoinitiation was performed by light irradiation. At about 25 seconds after light irradiation, gel was generated from the surface, and at 50 seconds, bubble formation and polymerization occurred at the same time. Then, the reaction was allowed for additional 3 minutes, and the polymerized sheet was taken to measure gel strength of the polymerized hydrogel.

The polymerized sheet was cut in a size of 3 cm×3 cm, and then subjected to a chopping process using a meat chopper having a perforated panel of a pore size of 8 mm to prepare crumbs.

The crumbs were dried in an oven capable of shifting airflow up and down. The crumbs were uniformly dried by flowing hot air at 180° C. from the bottom to the top for 20 minutes and from the top to the bottom for 20 minutes. After drying, the dried product had a water content of 2% or less.

After drying, the product was pulverized using a pulverizer and sorted by size, and a size of about 150 to about 850 μm was selected to prepare a base polymer.

Thereafter, 100 g of the base polymer was mixed with 5 g of water, 2 g of ethylene carbonate, and 0.5 g of aluminium sulfate ($Al_2SO_4$), and surface crosslinking reaction was allowed at 190° C. for 50 minutes. After pulverization, a surface-treated superabsorbent polymer having a particle size of 150 to 850 μm was obtained by using a sieve.

Example 2

A superabsorbent polymer was prepared in the same manner as in Example 1, except that 55 g of 5 wt % polyethylene glycol diacrylate diluted with acrylic acid was used instead of 50 g thereof, and 11 g of 5 wt % 1,6-hexanediol diacrylate diluted with acrylic acid was used instead of 10 g thereof in Example 1.

Example 3

A superabsorbent polymer was prepared in the same manner as in Example 1, except that 46 g of 5 wt % polyethylene glycol diacrylate diluted with acrylic acid was used instead of 50 g thereof, and 9 g of 5 wt % 1,6-hexanediol diacrylate diluted with acrylic acid was used instead of 10 g thereof in Example 1.

Example 4

A superabsorbent polymer was prepared in the same manner as in Example 1, except that a meat chopper having a perforated panel of a hole size of 6.5 mm was used instead of the meat chopper having a perforated panel of a hole size of 8 mm in Example 1.

Example 5

A superabsorbent polymer was prepared in the same manner as in Example 1, except that a meat chopper having a perforated panel of a hole size of 10 mm was used instead of the meat chopper having a perforated panel of a hole size of 8 mm in Example 1.

Comparative Example 1

A superabsorbent polymer was prepared in the same manner as in Example 1, except that 62 g of 5 wt % polyethylene glycol diacrylate diluted with acrylic acid was used instead of 50 g thereof, and 21 g of 5 wt % 1,6-hexanediol diacrylate diluted with acrylic acid was used instead of 10 g thereof in Example 1.

Comparative Example 2

A superabsorbent polymer was prepared in the same manner as in Example 1, except that 31 g of 5 wt % polyethylene glycol diacrylate diluted with acrylic acid was used instead of 50 g thereof, and 5 wt % 1,6-hexanediol diacrylate diluted with acrylic acid was not used in Example 1.

Comparative Example 3

A superabsorbent polymer was prepared in the same manner as in Example 1, except that 62 g of 5 wt % polyethylene glycol diacrylate diluted with acrylic acid was used instead of 50 g thereof, 21 g of 5 wt % 1,6-hexanediol diacrylate diluted with acrylic acid was used instead of 10 g thereof, and a meat chopper having a perforated panel of a hole size of 16 mm was used instead of the meat chopper having a perforated panel of a hole size of 8 mm in Example 1.

Comparative Example 4

A superabsorbent polymer was prepared in the same manner as in Example 1, except that 31 g of 5 wt % polyethylene glycol diacrylate diluted with acrylic acid was used instead of 50 g thereof, 5 wt % 1,6-hexanediol diacrylate diluted with acrylic acid was not used, and a meat chopper having a perforated panel of a hole size of 16 mm was used instead of the meat chopper having a perforated panel of a hole size of 8 mm in Example 1.

Comparative Example 5

A superabsorbent polymer was prepared in the same manner as in Example 1, except that a meat chopper having a perforated panel of a hole size of 16 mm was used instead of the meat chopper having a perforated panel of a hole size of 8 mm in Example 1.

The main process conditions of Examples 1 to 5 and Comparative Examples 1 to 5 are given in the following Table 2.

TABLE 2

| | Type and concentration of internal crosslinking agent | Diameter of hole in coarse pulverization step (unit: mm) |
|---|---|---|
| Example 1 | PEGDA 4,800 ppm, HDDA 1,000 ppm | 8 |
| Example 2 | PEGDA 5,300 ppm, HDDA 1,000 ppm | 8 |
| Example 3 | PEGDA 4,500 ppm, HDDA 900 ppm | 8 |
| Example 4 | PEGDA 4,800 ppm, HDDA 1,000 ppm | 6.5 |
| Example 5 | PEGDA 4,800 ppm, HDDA 1,000 ppm | 10 |
| Comparative Example 1 | PEGDA 6,000 ppm, HDDA 2,000 ppm | 8 |
| Comparative Example 2 | PEGDA 3,000 ppm | 8 |
| Comparative Example 3 | PEGDA 6,000 ppm, HDDA 2,000 ppm | 16 |
| Comparative Example 4 | PEGDA 3,000 ppm | 16 |
| Comparative Example 5 | PEGDA 4,800 ppm, HDDA 1,000 ppm | 16 |

* In Table 1, PEGDA represents polyethyleneglycol diacrylate, and HDDA represents 1,6-hexanediol diacrylate.
* The concentration of each internal crosslinking agent was expressed as a concentration (ppm) with respect to the total weight of acrylic acid included in the monomer composition.

Experimental Example

Physical properties of the superabsorbent polymers prepared in Examples 1 to 5 and Comparative Examples 1 to 5 were evaluated as follows, and the physical properties thus measured are shown in the following Table 3.

(1) Gel Strength

With regard to the hydrogel polymers obtained by the methods of preparing superabsorbent polymers of Examples 1 to 5 and Comparative Examples 1 to 5, gel strength was measured according to the following method.

First, 30 g of the hydrogel polymer samples obtained after polymerization were weighed. Each sample thus weighed was sufficiently swollen in 300 g of 0.9% NaCl solution for 1 hour. The hydrogel polymer was cut in a size of 5 mm×5 mm×5 mm, and then maintained in a closed container until ready for testing.

Before placing the hydrogel polymer between the parallel plates of the rheometer, it was blotted on filter paper to be sure that no free water is present between the particles during testing.

2 g of the swollen hydrogel polymer was measured by using a Rheometer. In this regard, rheometry was performed under the experimental conditions of Plate Gap Size of 2 mm; Strain amplitude of 1%; Oscillation frequency of 10 radian/sec; ambient temperature of 22° C.; plate of 25 mm, TA Instruments-AR Series. After measured for 5 minutes, the average value was taken as the measured value.

(2) Centrifuge Retention Capacity (CRC)

Retention capacity by absorbency under no load was measured for the superabsorbent polymers of Examples 1 to 5 and Comparative Examples 1 to 5 according to EDANA WSP 241.2 (European Disposables and Nonwovens Association, EDANA).

That is, the obtained superabsorbent polymer $W_0$ (g, about 0.2 g) was uniformly placed into a nonwoven-fabric-made bag, followed by sealing. Then, the bag was immersed into 0.9% by weight of physiological saline solution at room temperature. 30 minutes later, the bag was drained at 250 G for 3 minutes with a centrifuge, and the weight $W_2(g)$ of the bag was then measured. Further, the same procedure was carried out using no superabsorbent polymer, and the resultant weight $W_1(g)$ was measured.

These weights thus obtained were used to calculate CRC (g/g) according to the following Equation 1 to confirm centrifuge retention capacity.

$$CRC(g/g)=\{[W_2(g)-W_1(g)]/W_0(g)\}-1 \quad \text{[Equation 1]}$$

wherein $W_0(g)$ is the weight (g) of the superabsorbent polymer, $W_1(g)$ is the weight of the apparatus which is measured after draining water off at 250 G for 3 minutes with a centrifuge using no superabsorbent polymer, and $W_2(g)$ is the weight of the apparatus including the superabsorbent polymer, which is measured after immersing the superabsorbent polymer in 0.9% by weight of the physiological saline solution at room temperature for 30 minutes and draining water off at 250 G for 3 minutes with a centrifuge.

(3) Absorbency Under Load (AUL)

Absorbency under load (AUL) of 0.9 psi was measured for the superabsorbent polymers of Examples 1 to 5 and Comparative Examples 1 to 5 according to EDANA WSP 242.2 (European Disposables and Nonwovens Association, EDANA).

First, a 400 mesh stainless steel net was installed in the bottom of the plastic cylinder having the internal diameter of 25 mm. Each of the superabsorbent polymers $W_0$ (g, 0.16 g) obtained in Examples 1 to 5 and Comparative Examples 1 to 5 was uniformly scattered on the steel net at the room temperature and the humidity of 50%, and a piston which may provide a load of 5.1 kPa (0.9 psi) uniformly was put thereon, in which the external diameter of the piston was slightly smaller than 25 mm, there was no gab between the internal wall of the cylinder and the piston, and the jig-jog of the cylinder was not interrupted. At this time, the weight $W_3(g)$ of the device was measured.

After putting a glass filter having a diameter of 90 mm and a thickness of 5 mm in a petri dish having a diameter of 150 mm, a physiological saline solution composed of 0.90% by weight of sodium chloride was poured in the dish until the surface level became equal to the upper surface of the glass filter. A sheet of filter paper having a diameter of 90 mm was put thereon. The measuring device was put on the filter paper and the solution was absorbed for 1 hour under the load. After 1 hr, the weight $W_4(g)$ was measured after lifting the measuring device up.

The weights thus obtained were used to calculate AUL (g/g) according to the following Equation 2, thereby confirming absorbency under load.

$$AUL(g/g)=[W_4(g)-W_3(g)]/W_0(g) \quad \text{[Equation 2]}$$

wherein $W_0(g)$ is the weight (g) of the superabsorbent polymer, $W_3(g)$ is the sum of the weight of the superabsorbent polymer and the weight of the apparatus capable of providing a load for the superabsorbent polymer, and $W_4(g)$ is the sum of the weight of the water-absorbed superabsorbent polymer after supplying water for the superabsorbent polymer under a load (0.9 psi) for 1 hour, and the weight of the apparatus capable of providing a load for the superabsorbent polymer.

(4) Absorption Rate (FSR: Free Swell Rate)

Absorption rate (FSR) was measured for the superabsorbent polymers of Examples 1 to 5 and Comparative Examples 1 to 5 according to a method described in International Patent Publication NO. WO 2009/016055.

(5) Liquid Permeability (SFC: Saline Flow Conductivity)

Liquid permeability (SFC) was measured for the superabsorbent polymers of Examples 1 to 5 and Comparative Examples 1 to 5 according to a method described in U.S. Pat. No. 5,669,894.

TABLE 3

|  | Hydrogel polymer strength (unit: Pa) | Centrifuge retention capacity (CRC) (unit: g/g) | Absorbency under load (AUL) (unit: g/g) | Absorption rate (FSR) (unit: g/g/s) | Liquid permeability (SEC) (unit: $*10^{-7}$ $cm^3*sec/g$) |
|---|---|---|---|---|---|
| Example 1 | 12,252 | 27.5 | 23.8 | 0.37 | 103 |
| Example 2 | 12,509 | 27.4 | 23.6 | 0.39 | 110 |
| Example 3 | 10,796 | 28.4 | 24.2 | 0.35 | 95 |
| Example 4 | 12,252 | 26.6 | 24.2 | 0.41 | 118 |
| Example 5 | 12,252 | 28.5 | 24 | 0.28 | 97 |
| Comparative Example 1 | 14,106 | 22.1 | 22 | 0.22 | 120 |
| Comparative Example 2 | 9,117 | 32.4 | 25.4 | 0.23 | 8 |
| Comparative Example 3 | 14,106 | 23.2 | 22.5 | 0.18 | 123 |
| Comparative Example 4 | 9,117 | 34 | 25.2 | 0.17 | 9 |
| Comparative Example 5 | 12,252 | 28.1 | 21.8 | 0.17 | 78 |

As shown in Table 2, compared to Comparative Examples 1 to 5, Examples 1 to 5 of the present invention provide superior superabsorbent polymers having balanced physical properties, in which the superabsorbent polymers exhibit synergistic effects of showing excellent centrifuge retention capacity (CRC), absorbency under load (AUL), liquid permeability (SFC), and absorption rate (FSR) at the same time.

What is claimed is:

1. A method of preparing a superabsorbent polymer, the method comprising the steps of:
    performing thermal polymerization or photo-polymerization of a monomer composition comprising a water-soluble ethylene-based unsaturated monomer, an internal crosslinking agent, and a polymerization initiator to prepare a hydrogel polymer having a gel strength of 10,000 Pa to 13,000 Pa,
    wherein the internal crosslinking agent includes polyethyleneglycol diacrylate, and hexanediol diacrylate at a concentration of 4,000 ppm to 7,500 ppm, based on the total weight of the water-soluble ethylene-based unsaturated monomer comprised in the monomer composition;
    coarsely pulverizing the hydrogel polymer by extruding the hydrogel polymer through an outlet having holes;
    drying the coarsely pulverized hydrogel polymer;
    pulverizing the dried polymer; and mixing the pulverized polymer and a surface crosslinking agent to perform a surface crosslinking reaction of the mixture.

2. The method of claim 1, wherein the diameter of the holes and the gel strength of the hydrogel polymer satisfy the following Formula 1:

$$1140*x+730 \leq y < 600*x+8400 \qquad \text{[Formula 1]}$$

wherein x is the diameter of the hole (unit: mm) and y is the gel strength (unit: Pa) of the hydrogel polymer before coarse pulverization.

3. The method of claim 1, wherein the internal crosslinking agent is a compound having a cure dose of 80% to 200%, relative to a cure dose of the water-soluble ethylene-based unsaturated monomer.

4. The method of claim 1, wherein the internal crosslinking agent is a compound having a cure dose of 160 to 400 mJ/cm$^2$.

5. The method of claim 1, further comprising the step of classifying the pulverized polymer according to a particle size of 150 to 850 μm, before the step of performing surface crosslinking reaction of the pulverized polymer.

6. The method of claim 1, wherein the superabsorbent polymer has centrifuge retention capacity (CRC) of 25 g/g or more, absorbency under load (AUL) of 20 g/g or more, absorption rate (FSR) of 0.25 g/g/s or more, and liquid permeability (SFC) of 70*10$^{-7}$ cm$^3$*sec/g or more.

\* \* \* \* \*